(12) United States Patent
Codd et al.

(10) Patent No.: US 7,087,643 B2
(45) Date of Patent: Aug. 8, 2006

(54) CARBAMATE COMPOUNDS FOR USE IN PREVENTING OR TREATING NEUROPATHIC PAIN AND CLUSTER AND MIGRAINE HEADACHE-ASSOCIATED PAIN

(75) Inventors: Ellen C. Codd, Blue Bell, PA (US); Carlos R. Plata-Salaman, Ambler, PA (US); Boyu Zhao, Lansdale, PA (US)

(73) Assignee: Ortho-McNeil Pharmaceutical Inc., Raritan, NJ (US)

( * ) Notice: Subject to any disclaimer, the term of this patent is extended or adjusted under 35 U.S.C. 154(b) by 40 days.

(21) Appl. No.: 10/869,406

(22) Filed: Jun. 16, 2004

(65) Prior Publication Data

US 2004/0259944 A1    Dec. 23, 2004

Related U.S. Application Data

(62) Division of application No. 10/193,600, filed on Jul. 11, 2002, now abandoned.

(60) Provisional application No. 60/305,636, filed on Jul. 16, 2001.

(51) Int. Cl.
*A00N 47/10* (2006.01)
*A61K 31/27* (2006.01)

(52) U.S. Cl. .................. 514/483; 514/484; 514/489

(58) Field of Classification Search ............ 514/483, 514/484, 489
See application file for complete search history.

(56) References Cited

U.S. PATENT DOCUMENTS

| | | | |
|---|---|---|---|
| 3,265,728 A | 8/1966 | Bossinger et al. | |
| 3,313,692 A | 4/1967 | Bossinger et al. | |
| 5,698,588 A * | 12/1997 | Choi et al. ................. | 514/483 |
| 5,854,283 A * | 12/1998 | Choi et al. ................. | 514/483 |
| 6,103,759 A * | 8/2000 | Choi et al. ................. | 514/489 |
| 6,541,513 B1 | 4/2003 | Plata-Salaman et al. | |
| 6,562,867 B1 | 5/2003 | Plata-Salaman et al. | |
| 6,589,985 B1 | 7/2003 | Plata-Salaman et al. | |
| 6,815,464 B1 * | 11/2004 | Plata-Salaman et al. .... | 514/483 |

FOREIGN PATENT DOCUMENTS

| WO | WO 02/07822 A2 | 1/2002 |
|---|---|---|
| WO | WO 02 67922 A | 9/2002 |

OTHER PUBLICATIONS

Mulleners, W.M. et al., *Visual Cortex Excitability in Migraine With and Without Aura*, Headache, Jun. 2001, 41(6) 565-572.
Aurora, S.K, et al., *The Occipital Cortex is Hyperexcitable in Migraine: Experimental Evidence*, Headache, Jul.-Aug. 1999, 39(7), 469-476.
Brau, M.E. et al., *Effect of Drugs Used for Neuropathic Pain Management on Tetrodotoxin-resistant Na(+) Currents in Rat Sensory Neurons*, Anesthesiology, 2001, Jan. 94(1), 137-144.
Siddall, P.J. and Loeser, J.D., *Pain Following Spinal Cord Injury*, Spinal Cord, 2001, Feb. 39(2) 63-73.
Kontinen, V.K. et al., *Electrophysiologic Evidence for Increased Endogenous Gabaergic But Not Glycinergic Inhibitory Tone in the Rat Spinal Nerve Ligation Model of Neuropathy*, Anesthesiology, Feb. 2001, 94(2), 333-339.
Delvaux, F. & Schoenen, J., *New Generation Anti-Epileptics for Facial Pain and Headache*, Acta Neurol. Belg., Mar. 2001, 101(1), 42-46.
Johannessen, C.U., *Mechanisms of Action of Valproate: A Commentatory*, Neurochem. Int., 2000, Aug.-Sep., 37 (2-3), 103-110.
Magnus, L., *Nonepileptic Uses of Gabapentin*, Epilepsia, 1999, 40 Suppl 6, S66-72.
U.S. Appl. No. 09/906,251, Ortho-McNeil Pharmaceutical, Inc.
U.S. Appl. No. 10/081,606, Ortho-McNeil Pharmaceutical, Inc.

(Continued)

*Primary Examiner*—Johann Richter
*Assistant Examiner*—Chukwuma Nwaonicha
(74) *Attorney, Agent, or Firm*—Peter L. Herridge

(57) ABSTRACT

This invention is directed to a method for preventing or treating neuropathic pain and cluster and migraine headache-associated pain comprising administering to a subject in need thereof a therapeutically effective amount of a compound of Formula (I):

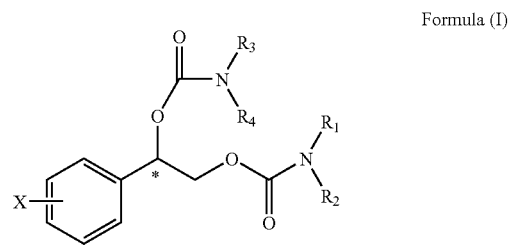

Formula (I)

wherein phenyl is substituted at X with one to five halogen atoms independently selected from the group consisting of fluorine, chlorine, bromine and iodine; and; $R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of hydrogen, halogen, $C_1$–$C_4$ alkyl, $C_1$–$C_4$ alkoxy, amino, nitro and cyano).

40 Claims, No Drawings

OTHER PUBLICATIONS

U.S. Appl. No. 10/081,713, Ortho-McNeil Pharmaceutical, Inc.
U.S. Appl. No. 10/081,943, Ortho-McNeil Pharmaceutical, Inc.
U.S. Appl. No. 10/192,973, Ortho-McNeil Pharmaceutical, Inc.
U.S. Appl. No. 10/081,764, Ortho-McNeil Pharmaceutical, Inc.
Hansen, "Treatment of Chronic Pain with Anitepileptic Drugs: A New Era", Southern Medical Journal, vol. 92, No. 7 (Jul. 1999). pp. 642-650.

* cited by examiner

CARBAMATE COMPOUNDS FOR USE IN PREVENTING OR TREATING NEUROPATHIC PAIN AND CLUSTER AND MIGRAINE HEADACHE-ASSOCIATED PAIN

CROSS REFERENCE TO RELATED APPLICATION

This application is a Divisional of U.S. application Ser. No. 10/193,600, filed Jul. 11, 2002 now abandoned which claims priority from U.S. provisional application Ser. No. 60/305,636 filed Jul. 16, 2001, the contents of which are hereby incorporated by reference.

FIELD OF THE INVENTION

This invention is directed to a method for use of a carbamate compound in preventing or treating neuropathic pain and cluster and migraine headache-associated pain. More particularly, this invention is directed to a method for use of a halogenated 2-phenyl-1,2-ethanediol dicarbamate compound for preventing or treating neuropathic pain and cluster and migraine headache-associated pain.

BACKGROUND OF THE INVENTION

The conditions grouped under the term neuropathic pain constitute an area of continuing medical need.

Neuropathic pain is defined as pain caused by aberrant somatosensory processing in the peripheral or central nervous system and includes painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathetic dystrophy, phantom limb syndrome and other chronic and debilitating condition-associated pain syndromes.

Cluster headache (also called Raeder's syndrome, histamine cephalalgia and sphenopalatine neuralgia) is characterized by a series of short-lived attacks of periorbital pain on an almost daily basis over a relatively short period of time (for example, over 4 to 8 weeks) followed by a pain-free interval. Migraine headache is also a periodic recurring disorder that can be associated with paroxysmal pain, vomiting, and photophobia. Migraine headaches include, and are not limited to, classic migraine (migraine with aura: associated with premonitory sensory, motor or visual symptoms) and common migraine (migraine without aura). Cluster and migraine headache-associated pain are also clinical indications with significant unmet medical need.

Neuropathic pain, migraine and cluster headache are all associated with changes in neuronal excitability (Mulleners W. M., et al, Visual Cortex Excitability in Migraine With and Without Aura, *Headache,* 2001, June, 41(6), 565–572; Aurora S. K., et al, The occipital cortex is hyperexcitable in migraine: experimental evidence, *Headache,* 1999, July–August, 39(7), 469–76; Brau M. E., et al, Effect of drugs used for neuropathic pain management on tetrodotoxin-resistant Na(+) currents in rat sensory neurons, *Anesthesiology,* 2001, January, 94(1), 137–44; Siddall P. J. and Loeser J. D., Pain following spinal cord injury, *Spinal Cord,* 2001, February, 39(2), 63–73; Kontinen V. K., et al, Electrophysiologic evidence for increased endogenous gabaergic but not glycinergic inhibitory tone in the rat spinal nerve ligation model of neuropathy, *Anesthesiology,* 2001, February, 94(2), 333–9). Various anti-epileptic drugs (AEDs) that stabilize neuronal excitability are effective in neuropathic pain and cluster and migraine headache-associated pain (Delvaux V. and Schoenen J., New generation anti-epileptics for facial pain and headache, *Acta Neurol. Belg.,* 2001, March, 101 (1), 42–46; Johannessen C. U., Mechanisms of action of valproate: a commentary, *Neurochem. Int.,* 2000, August–September, 37(2–3), 103–110 and Magnus L., Non-epileptic uses of gabapentin, *Epilepsia,* 1999, 40 Suppl 6, S66–72). Neuropathic pain and cluster and migraine headache-associated pain are widespread conditions that cause suffering.

Substituted phenyl alkyl carbamate compounds have been described in U.S. Pat. No. 3,265,728 to Bossinger, et al (hereby incorporated by reference), as useful in treating the central nervous system, having tranquilization, sedation and muscle relaxation properties of the formula:

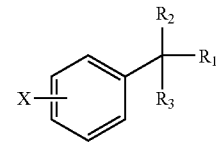

wherein $R_1$ is either carbamate or alkyl carbamate containing from 1 to 3 carbon atoms in the alkyl group; $R_2$ is either hydrogen, hydroxy, alkyl or hydroxy alkyl containing from 1 to 2 carbons; $R_3$ is either hydrogen or alkyl containing from 1 to 2 carbons; and X can be halogen, methyl, methoxy, phenyl, nitro or amino.

A method for inducing calming and muscle relaxation with carbamates has been described in U.S. Pat. No. 3,313,692 to Bossinger, et al (hereby incorporated by reference) by administering a compound of the formula:

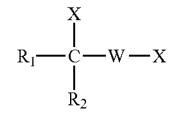

in which W represents an aliphatic radical containing less than 4 carbon atoms, wherein $R_1$ represents an aromatic radical, $R_2$ represents hydrogen or an alkyl radical containing less than 4 carbon atoms, and X represents hydrogen or hydroxy or alkoxy and alkyl radicals containing less than 4 carbon atoms or the radical:

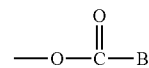

in which B represents an organic amine radical of the group consisting of heterocyclic, ureido and hydrazino radicals and the radical —$N(R_3)_2$ wherein $R_3$ represents hydrogen or an alkyl radical containing less than 4 carbon atoms.

Optically pure forms of halogen substituted 2-phenyl-1,2-ethanediol monocarbamates and dicarbamates have also been described in U.S. Pat. No. 6,103,759 to Choi, et al (hereby incorporated by reference), as effective for treating and preventing central nervous system disorders including convulsions, epilepsy, stroke and muscle spasm; and as useful in the treatment of central nervous system diseases, particularly as anticonvulsants, antiepileptics, neuroprotective agents and centrally acting muscle relaxants, of the formulae:

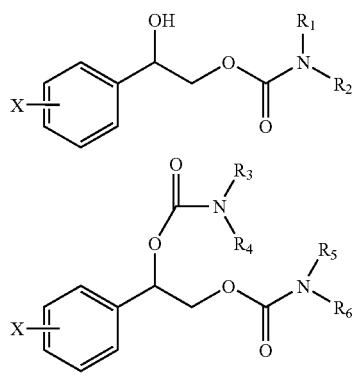

wherein one enantiomer predominates and wherein the phenyl ring is substituted at X with one to five halogen atoms selected from fluorine, chlorine, bromine or iodine atoms and $R_1$, $R_2$, $R_3$, $R_4$, $R_5$ and $R_6$ are each selected from hydrogen and straight or branched alkyl groups with one to four carbons optionally substituted with a phenyl group with substituents selected from the group consisting of hydrogen, halogen, alkyl, alkyloxy, amino, nitro and cyano. Pure enantiomeric forms and enantiomeric mixtures were described wherein one of the enantiomers predominates in the mixture for the compounds represented by the formulae above; preferably one of the enantiomers predominates to the extent of about 90% or greater; and, most preferably, about 98% or greater.

A halogen substituted 2-phenyl-1,2-ethanediol dicarbamate compound of Formula (I) has not been previously described as useful for preventing or treating neuropathic pain or cluster and migraine headache-associated pain.

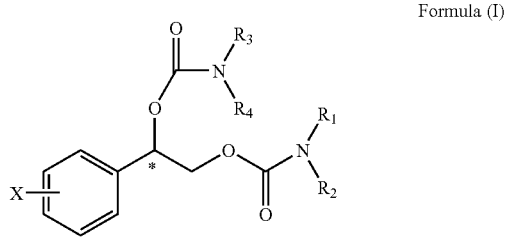

Formula (I)

Recent preclinical studies have revealed previously unrecognized pharmacological properties which suggest that a dicarbamate compound of Formula (I) is useful in preventing or treating neuropathic pain and cluster and migraine headache-associated pain. Therefore, it is an object of the present invention to teach a method for use of a dicarbamate compound of Formula (I) in preventing or treating neuropathic pain and cluster and migraine headache-associated pain.

SUMMARY OF THE INVENTION

The present invention is directed to a method for preventing or treating neuropathic pain and cluster and migraine headache-associated pain comprising administering to a subject in need thereof a therapeutically effective amount of a compound of Formula (I):

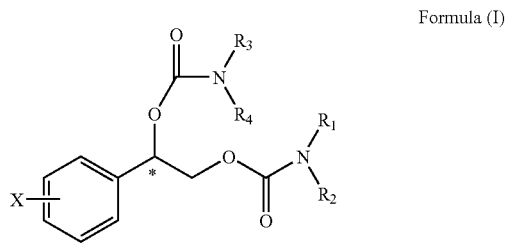

Formula (I)

wherein phenyl is substituted at X with one to five halogen atoms independently selected from the group consisting of fluorine, chlorine, bromine and iodine; and, $R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

Embodiments of the invention include a method for preventing or treating neuropathic pain; wherein neuropathic pain results from chronic or debilitating conditions comprising administering to a subject in need thereof a therapeutically effective amount of a pharmaceutical composition comprising a pharmaceutically acceptable carrier and a compound of Formula (I).

Embodiments of the invention include a method for preventing or treating cluster and migraine headache-associated pain comprising administering to a subject in need thereof a therapeutically effective amount of a pharmaceutical composition comprising a pharmaceutically acceptable carrier and a compound of Formula (I).

Embodiments of the method include the use of a compound of Formula (I) for the preparation of a medicament for preventing or treating neuropathic pain and cluster and migraine headache-associated pain in a subject in need thereof.

Embodiments of the method include the use of a racemic mixture of a compound of Formula (I), an enantiomer of Formula (I) or an enantiomeric mixture wherein an enantiomer of Formula (I) predominates. For an enantiomeric mixture wherein an enantiomer of Formula (I) predominates, preferably, an enantiomer of Formula (I) predominates to the extent of about 90% or greater. More preferably, an enantiomer of Formula (I) predominates to the extent of about 98% or greater.

DETAILED DESCRIPTION OF THE INVENTION

The present invention is directed to a method for preventing or treating neuropathic pain and cluster and migraine headache-associated pain comprising administering to a subject in need thereof a therapeutically effective amount of a compound of Formula (I):

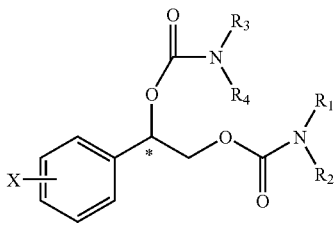

Formula (I)

wherein
phenyl is substituted at X with one to five halogen atoms independently selected from the group consisting of fluorine, chlorine, bromine and iodine; and, $R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of a compound of Formula (I) wherein X is chlorine; preferably, X is substituted at the ortho position of the phenyl ring.

The present method also includes the use of a compound of Formula (I) wherein $R_1$, $R_2$, $R_3$ and $R_4$ are preferably selected from hydrogen.

An embodiment of the present method includes the use of a racemic mixture of a compound of Formula (I), an enantiomer of Formula (I) or an enantiomeric mixture wherein an enantiomer of Formula (I) predominates wherein X is chlorine; preferably, X is substituted at the ortho position of the phenyl ring.

The present method also includes the use of a racemic mixture of a compound of Formula (I), an enantiomer of Formula (I) or an enantiomeric mixture wherein an enantiomer of Formula (I) predominates wherein $R_1$, $R_2$, $R_3$ and $R_4$ are preferably selected from hydrogen.

For an enantiomeric mixture wherein an enantiomer of Formula (I) predominates, preferably, an enantiomer of Formula (I) predominates to the extent of about 90% or greater. More preferably, an enantiomer of Formula (I) predominates to the extent of about 98% or greater.

An embodiment of the present method includes a method for preventing or treating neuropathic pain and cluster and migraine headache-associated pain comprising administering to a subject in need thereof a therapeutically effective amount of a compound of Formula (Ia):

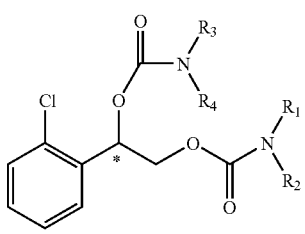

Formula (Ia)

wherein
$R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of a compound of Formula (Ia) wherein $R_1$, $R_2$, $R_3$ and $R_4$ are preferably selected from hydrogen.

An embodiment of the present method includes the use of a racemic mixture of a compound of Formula (Ia), an enantiomer of Formula (Ia) or an enantiomeric mixture wherein an enantiomer of Formula (Ia) predominates wherein X is chlorine; preferably, X is substituted at the ortho position of the phenyl ring.

The present method also includes the use of a racemic mixture of a compound of Formula (Ia), an enantiomer of Formula (Ia) or an enantiomeric mixture wherein an enantiomer of Formula (Ia) predominates wherein $R_1$, $R_2$, $R_3$ and $R_4$ are preferably selected from hydrogen.

For an enantiomeric mixture wherein an enantiomer of Formula (Ia) predominates, preferably, an enantiomer of Formula (Ia) predominates to the extent of about 90% or greater. More preferably, an enantiomer of Formula (Ia) predominates to the extent of about 98% or greater.

An embodiment of the present method includes a method for preventing or treating neuropathic pain and cluster and migraine headache-associated pain comprising administering to a subject in need thereof a therapeutically effective amount of a compound of Formula (Ib):

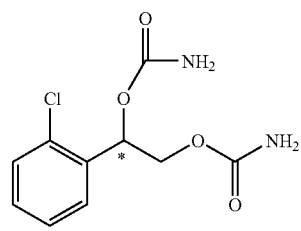

Formula (Ib)

An embodiment of the present method includes the use of a racemic mixture of a compound of Formula (Ib), an enantiomer of Formula (Ib) or an enantiomeric mixture wherein an enantiomer of Formula (Ib) predominates.

For an enantiomeric mixture wherein an enantiomer of Formula (Ib) predominates, preferably, an enantiomer of Formula (Ib) predominates to the extent of about 90% or greater. More preferably, an enantiomer of Formula (Ib) predominates to the extent of about 98% or greater.

An embodiment of the present method includes a method for preventing or treating neuropathic pain and cluster and migraine headache-associated pain comprising administering to a subject in need thereof a therapeutically effective amount of an enantiomer of Formula (Ic) or an enantiomeric mixture wherein the enantiomer of Formula (Ic) predominates:

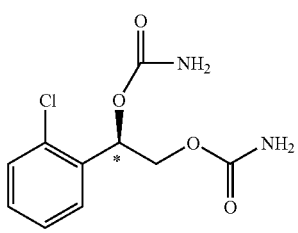

Formula (Ic)

For an enantiomeric mixture wherein the enantiomer of Formula (Ic) predominates, preferably, the enantiomer of Formula (Ic) predominates to the extent of about 90% or greater. More preferably, the enantiomer of Formula (Ic) predominates to the extent of about 98% or greater.

Other crystal forms of an enantiomer of Formula (I) may exist and as such are intended to be included in the present invention.

It is apparent to those skilled in the art that the compounds of the invention are present as a racemic mixture, enantiomers and enantiomeric mixtures thereof. A carbamate compound selected from the group consisting of Formula (I), Formula (Ia), Formula (Ib) and Formula (Ic) contains an asymmetric chiral carbon atom at the benzylic position, which is the aliphatic carbon adjacent to the phenyl ring (represented by the asterisk in the structural formulae).

Compounds of the present invention may be prepared as described in the previously referenced Bossinger '728 patent (incorporated by reference), Bossinger '692 patent (incorporated by reference) and Choi '759 patent (incorporated by reference).

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The present invention contemplates a method for preventing or treating neuropathic pain and cluster and migraine headache-associated pain in a subject in need thereof comprising administering to the subject a therapeutically effective amount of a compound of Formula (I).

An embodiment of the present invention includes a method for preventing or treating neuropathic pain resulting from chronic or debilitating conditions in a subject in need thereof. The chronic or debilitating conditions that lead to neuropathic pain include, but are not limited to, painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathetic dystrophy, phantom limb syndrome and other chronic and debilitating condition-associated pain syndromes.

An embodiment of the present invention also includes a method for preventing or treating cluster and migraine headache-associated pain in a subject in need thereof. Cluster headache-associated pain is characterized by a series of short-lived attacks on an almost daily basis over a relatively short period of time followed by a pain-free interval. Migraine headache-associated pain is characterized by blinding pain, vomiting, photophobia and recurrence at regular interval; and, includes, but is not limited to, classic migraine headache-associated pain (migraine with aura) and common migraine headache-associated pain (migraine without aura).

An embodiment of the invention also includes a method for slowing or delaying the progression of neuropathic pain and cluster and migraine headache-associated pain in a subject in need thereof comprising administering to the subject a therapeutically effective amount of a compound of Formula (I).

The term "slowing or delaying the progression of" neuropathic pain and cluster and migraine headache-associated pain is intended to include minimizing the severity, duration and frequency of the clinical manifestations associated with neuropathic pain and cluster and migraine headache-associated pain in a subject.

An example of the method of the present invention comprises administering to the subject a therapeutically effective amount of a compound of Formula (I) in a pharmaceutical composition comprising a pharmaceutically acceptable carrier and a compound of Formula (I). The method of the present invention also includes the use of a compound of Formula (I) for the preparation of a medicament for preventing or treating neuropathic pain and cluster and migraine headache-associated pain.

Another example of the method of the present invention comprises administering to the subject a therapeutically effective amount of a compound of Formula (I) or pharmaceutical composition thereof in combination with one or more agents useful in preventing or treating neuropathic pain and cluster and migraine headache-associated pain.

A compound of Formula (I) or pharmaceutical composition thereof may be administered by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or peri-spinal routes of administration by delivery via intracranial or intravertebral needles or catheters with or without pump devices. It will be readily apparent to those skilled in the art that any dose or frequency of administration that provides the therapeutic effect described herein is suitable for use in the present invention.

The therapeutically effective amount of a compound of Formula (I) or pharmaceutical composition thereof may be from about 0.01 mg/Kg/dose to about 100 mg/Kg/dose. Preferably, the therapeutically effective amount may be from about 0.01 mg/Kg/dose to about 25 mg/Kg/dose. More preferably, the therapeutically effective amount may be from about 0.01 mg/Kg/dose to about 10 mg/Kg/dose. Most preferably, the therapeutically effective amount may be from about 0.01 mg/Kg/dose to about 5 mg/Kg/dose. Therefore, the therapeutically effective amount of the active ingredient contained per dosage unit (e.g., tablet, capsule, powder, injection, suppository, teaspoonful and the like) as described herein may be from about 1 mg/day to about 7000 mg/day for a subject, for example, having an average weight of 70 Kg.

The dosages, however, may be varied depending upon the requirement of the subjects (including factors associated with the particular subject being treated, including subject age, weight and diet, strength of the preparation, the advancement of the disease condition and the mode and time of administration).

Optimal dosages to be administered may be readily determined by those skilled in the art and will result in the need to adjust the dose to an appropriate therapeutic level. The use of either daily administration or post-periodic dosing may be employed. Preferably, a compound of Formula (I) or pharmaceutical composition thereof is administered orally or parenterally. More preferably, a compound of Formula (I) or pharmaceutical composition thereof is administered orally.

In accordance with the methods of the present invention, a compound of Formula (I) or pharmaceutical composition thereof described herein may be administered separately, at different times during the course of therapy or concurrently in divided combination or single combination forms. Advantageously, a compound of Formula (I) or pharmaceutical composition thereof may be administered in a single daily dose or the total daily dosage may be administered via continuous delivery or in divided doses of two, three or four times daily. The instant invention is therefore to be understood as embracing all such methods and regimes of simultaneous or alternating treatment and the term "administering" is to be interpreted accordingly.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system (preferably, an animal; more preferably, a mammal; most preferably, a human) that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare a pharmaceutical composition of the present invention, a compound of Formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1–3, edited by Lieberman et al; *Pharmaceutical Dosage Forms: Parenteral Medications*, Volumes 1–2, edited by Avis et al; and *Pharmaceutical Dosage Forms: Disperse Systems*, Volumes 1–2, edited by Lieberman et al; published by Marcel Dekker, Inc.

Preferably a pharmaceutical composition is in a unit dosage form such as a tablet, pill, capsule, caplet, gelcap, lozenge, granule, powder, sterile parenteral solution or suspension, metered aerosol or liquid spray, drop, ampoule, autoinjector device or suppository for administration by oral, intranasal, sublingual, intraocular, transdermal, parenteral, rectal, vaginal, inhalation or insufflation means. Alternatively, the composition may be presented in a form suitable for once-weekly or once-monthly administration or may be adapted to provide a preparation for intramuscular injection.

In preparing a pharmaceutical composition having a solid dosage form for oral administration, such as a tablet, pill, capsule, caplet, gelcap, lozenge, granule or powder (each including immediate release, timed release and sustained release formulations), suitable carriers and additives include but are not limited to diluents, granulating agents, lubricants, binders, glidants, disintegrating agents and the like. If desired, tablets may be sugar coated, gelatin coated, film coated or enteric coated by standard techniques.

For preparing a solid dosage form, the principal active ingredient is mixed with a pharmaceutical carrier (e.g. conventional tableting ingredients such as diluents, binders, adhesives, disintegrants, lubricants, antiadherents and glidants). Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

In preparing a pharmaceutical composition having a liquid dosage form for oral, topical and parenteral administration, any of the usual pharmaceutical media or excipients may be employed. Thus, for liquid unit dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form. The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

BIOLOGICAL EXPERIMENTAL EXAMPLES

The activity of a compound Formula (I) for use in the treatment of neuropathic pain was evaluated in the following experimental examples and is intended to be a way of illustrating but not limiting the invention.

The procedure used to test the antiallodynic activity of a compound of Formula (I) was the procedure for the measurement of allodynia found in the Chung Model (Kim S. H. and Chung J. M., An Experimental Model for Peripheral Neuropathy Produced by Segmental Spinal Nerve Ligation in the Rat, *Pain*, 1992, 50, 355–363).

Example 1

Evaluation of Antiallodynic Activity (Manually Applied Von Frey Probes)

Animals

Pathogen-free, male albino Sprague-Dawley rats, 200 g, were purchased from Harlan Industries (Indianapolis, Ind.)

and maintained on a 12-h light/dark cycle (lights on at 06:00 h) in a climate-controlled room with food and water available ad libitum up to the time of the testing and food withdrawn 18 hr prior to testing.

Surgical Procedure and Measurement of Allodynia

The rats were anesthetized with isoflurane inhalant anesthesia. The left lumbar spinal nerve at the level of L5 was tightly ligated (4-0 silk suture) distal to the dorsal root ganglion and prior to entrance into the sciatic nerve, as described by Kim and Chung. The incisions were closed and the rats were allowed to recover under conditions described above. This procedure results in mechanical allodynia in the left hind paw. The sham operation, when performed, consisted of a similar surgical procedure lacking only the final ligation of the spinal nerve. Mechanical (tactile) allodynia was assessed by recording the pressure at which the affected paw (ipsilateral to the site of nerve injury) was withdrawn from graded stimuli (von Frey filaments ranging from 4.0 to 148.1 mN) applied by hand perpendicularly to the plantar surface of the paw (between the footpads) through wire-mesh observation cages. A paw withdrawal threshold (PWT) was determined by sequentially increasing and decreasing the stimulus strength and analyzing withdrawal data using a Dixon non-parametric test, as described by Chaplan et al (Chaplan S. R., Bach F. W., Pogrel J. W., Chung J. M. and Yaksh T. L., Quantitative Assessment of Tactile Allodynia in the Rat Paw, *J Neurosci Meth*, 1994, 53, 55–63). Normal rats, sham operated rats, and the contralateral paw of L5 ligated rats withstand at least 148.1 mN (equivalent to 15 g) of pressure without responding. Spinal nerve ligated rats respond to as little as 4.0 mN (equivalent to 0.41 g) of pressure on the affected paw. Rats were included in the study only if they did not exhibit motor dysfunction (e.g., paw dragging or dropping) and their PWT was below 39.2 mN (equivalent to 4.0 g). The PWT was used to calculate the % maximal possible effect (% MPE) according to the formula:

$$\%MPE=100\times(PWT-CT)/(CO-CT).$$

Data Analysis

As summarized in Table 1 below, the enantiomer of Formula (Ic) was screened for antiallodynic activity in the Chung model of neuropathic pain at a dose of 30 and 100 mg/Kg, po, with responses being measured at 0.5, 1, 2 and 4 hours post dosing; responses returned to baseline by one hour. Data for 30 mg/Kg is at the time of peak effect, 30 minutes after oral dosing, with n=5 animals per dose. Data for 100 mg/Kg is at the time of peak effect, 30 to 60 minutes after oral dosing, with n=10 animals per dose.

TABLE 1

Antiallodynic Effect Assessed with Manually Applied Von Frey Probes

| Dose (mg/Kg) | % Maximum Possible Effect | n |
|---|---|---|
| 30 | 0 | 5 |
| 100 | 25.7 | 10 |

Example 2

Evaluation of Antiallodynic Activity (Electronic Von Frey Probes)

Animals

Pathogen-free, male Rj: Wistar (Han) rats (300–380 g) were purchased from Elevage Janvier, 53940 Le Genest-Saint-Isle, France. The animals were maintained on a 12-h light/dark cycle (lights on from 7:00–19:00) in a controlled ambient temperature of 21±1° C., and relative humidity maintained at 40–70%. The animals had free access to food (UAR 113) and tap water until tested.

Surgical Procedure

Rats were anesthetized (sodium pentobarbital 40 mg/kg i.p.). A ligature was tied tightly around the left L5 and L6 spinal nerves. The rats received an i.m. injection of 50 000 IU Penicillin (Diamant®) and were allowed to recover. This procedure results in mechanical allodynia in the left hind paw. Two weeks after the surgery, when the allodynic state was fully developed, rats submitted consecutively to tactile stimulation of both the non-lesioned and the lesioned hindpaws.

Measurement of Allodynia

The animals were placed on an elevated grid floor in Plexiglass boxes (19×11.5×13 cm). The tip of an electronic Von Frey probe (Bioseb, Model 1610) was then applied with increasing pressure to the lesioned and non-lesioned hindpaws and the force required to induce paw-withdrawal was automatically recorded. Prior to receiving drug treatment all animals were submitted to tactile stimulation and assigned to treatment groups matched on the basis of their pain response. This procedure was carried out 3 times for each paw and the mean paw force was calculated to provide basic scores per animal. Data were expressed as percent change (means±SEM) of effectiveness from the controls. Statistical analysis was done using non-paired and paired Student's t tests.

Drug Administration and Testing Schedule

As summarized in Table 2 below, the enantiomer of Formula (Ic) was evaluated at the doses 10, 30 and 100 mg/kg (n=8), administered p.o. in a volume of 5 mL/kg. Morphine (128 mg/kg) was used as reference substance. Control animals received a p.o. administration of vehicle. The test was performed blind 30, 60 and 90 minutes after drug administration.

Data Analysis

The enantiomer of Formula (Ic) non-dose-dependently increased the force required to induce paw-withdrawal in the ligatured paw in response to tactile stimulation at the 60 minute post-dosing measurement without affecting the non-ligatured paw. These effects were significant at all three doses (10, 30 and 100 mg/Kg) tested and appeared more marked than that observed with the morphine positive control (38% change at 128 mg/Kg morphine). This significant anti-allodynic effect of the enantiomer of Formula (Ic) was no longer present by 90 minutes post-dosing (ns: p value is not significant).

TABLE 2

Antiallodynic Activity Electronic Von Frey Probes

| Dose (mg/Kg) | % Change | n | p |
|---|---|---|---|
| 0 | 0 | 8 | — |
| 10 | 69 | 8 | <0.05 |
| 30 | 115 | 8 | <0.01 |
| 100 | 88 | 8 | <0.01 |

What is claimed is:

1. A method for treating neuropathic pain and cluster headache-associated pain comprising administering to a subject in need thereof a therapeutically effective amount of a compound of Formula (I):

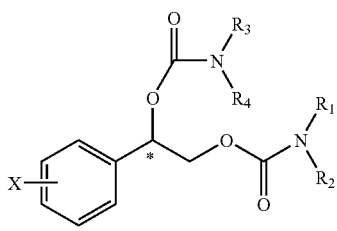

Formula (I)

wherein
phenyl is substituted at X with one to five halogen atoms independently selected from the group consisting of fluorine, chlorine, bromine and iodine; and,
$R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

2. A method for treating neuropathic pain comprising administering to a subject in need thereof a therapeutically effective amount of a compound of Formula (I):

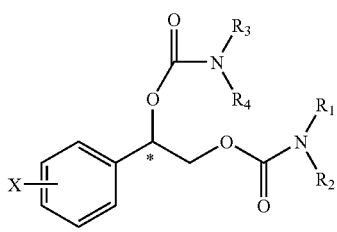

Formula (I)

wherein
phenyl is substituted at X with one to five halogen atoms independently selected from the group consisting of fluorine, chlorine, bromine and iodine; and,
$R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

3. A method for treating cluster headache-associated pain comprising administering to a subject in need thereof a therapeutically effective amount of a compound of Formula (I):

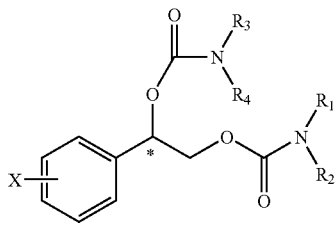

Formula (I)

wherein
phenyl is substituted at X with one to five halogen atoms independently selected from the group consisting of fluorine, chlorine, bromine and iodine; and,
$R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

4. The method of claim 1 wherein X is chlorine.

5. The method of claim 1 wherein X is substituted at the ortho position of the phenyl ring.

6. The method of claim 1 wherein $R_1$, $R_2$, $R_3$ and $R_4$ are selected from hydrogen.

7. The method of claim 1 wherein the compound of Formula (I) is selected from the group consisting of a racemic mixture of a compound of Formula (I), an enantiomer of a compound of Formula (I) and an enantiomeric mixture wherein an enantiomer of a compound of Formula (I) predominates.

8. The method of claim 7 wherein an enantiomer of Formula (I) predominates to the extent of about 90% or greater.

9. The method of claim 7 wherein an enantiomer of Formula (I) predominates to the extent of about 98% or greater.

10. The method of claim 1 wherein the compound of Formula (I) is a compound of Formula (Ia):

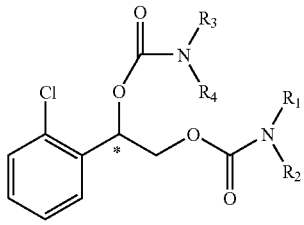

Formula (Ia)

wherein
$R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

11. The method of claim 10 wherein $R_1$, $R_2$, $R_3$ and $R_4$ are selected from hydrogen.

12. The method of claim 10 wherein the compound of Formula (Ia) is selected from the group consisting of a racemic mixture of a compound of Formula (Ia), an enantiomer of a compound of Formula (Ia) and an enantiomeric mixture wherein an enantiomer of a compound of Formula (Ia) predominates.

13. The method of claim 12 wherein an enantiomer of Formula (Ia) predominates to the extent of about 90% or greater.

14. The method of claim 12 wherein an enantiomer of Formula (Ia) predominates to the extent of about 98% or greater.

15. The method of claim 1 wherein the compound of Formula (I) is a compound of Formula (Ib):

[Formula (Ib) structure]

16. The method of claim 15 wherein the compound of Formula (Ib) is selected from the group consisting of a racemic mixture of the compound of Formula (Ib), an enantiomer of the compound of Formula (Ib) and an enantiomeric mixture wherein an enantiomer of the compound of Formula (Ib) predominates.

17. The method of claim 16 wherein an enantiomer of Formula (Ib) predominates to the extent of about 90% or greater.

18. The method of claim 16 wherein an enantiomer of Formula (Ib) predominates to the extent of about 98% or greater.

19. The method of claim 1 wherein the compound of Formula (I) is an enantiomer of Formula (Ic) or an enantiomeric mixture wherein the enantiomer of Formula (Ic) predominates:

[Formula (Ic) structure]

20. The method of claim 19 wherein the enantiomer of Formula (Ic) predominates to the extent of about 90% or greater.

21. The method of claim 19 wherein the enantiomer of Formula (Ic) predominates to the extent of about 98% or greater.

22. The method of claim 2 wherein the compound of Formula (I) is a compound of Formula (Ib):

[Formula (Ib) structure]

23. The method of claim 22 wherein the compound of Formula (Ib) is selected from the group consisting of a racemic mixture of the compound of Formula (Ib), an enantiomer of the compound of Formula (Ib) and an enantiomeric mixture wherein an enantiomer of the compound of Formula (Ib) predominates.

24. The method of claim 23 wherein an enantiomer of Formula (Ib) predominates to the extent of about 90% or greater.

25. The method of claim 23 wherein an enantiomer of Formula (Ib) predominates to the extent of about 98% or greater.

26. The method of claim 2 wherein the compound of Formula (I) is an enantiomer of Formula (Ic) or an enantiomeric mixture wherein the enantiomer of Formula (Ic) predominates:

[Formula (Ic) structure]

27. The method of claim 26 wherein the enantiomer of Formula (Ic) predominates to the extent of about 90% or greater.

28. The method of claim 26 wherein the enantiomer of Formula (Ic) predominates to the extent of about 98% or greater.

29. The method of claim 2 wherein neuropathic pain results from chronic or debilitating conditions.

30. The method of claim 29 wherein the chronic or debilitating conditions are selected from the group consisting of painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathetic dystrophy, phantom limb syndrome and other chronic and debilitating condition-associated pain syndromes.

31. The method of claim 26 wherein the therapeutically effective amount is from about 0.01 mg/Kg/dose to about 100 mg/Kg/dose.

32. The method of claim 3 wherein the compound of Formula (I) is a compound of Formula (Ib):

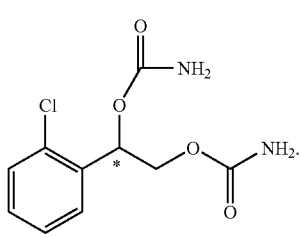

Formula (Ib)

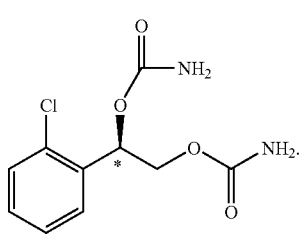

Formula (Ic)

33. The method of claim 32 wherein the compound of Formula (Ib) is selected from the group consisting of a racemic mixture of the compound of Formula (Ib), an enantiomer of the compound of Formula (Ib) and an enantiomeric mixture wherein an enantiomer of the compound of Formula (Ib) predominates.

34. The method of claim 3 wherein an enantiomer of Formula (Ib) predominates to the extent of about 90% or greater.

35. The method of claim 3 wherein an enantiomer of Formula (Ib) predominates to the extent of about 98% or greater.

36. The method of claim 3 wherein the compound of Formula (I) is an enantiomer of Formula (Ic) or an enantiomeric mixture wherein the enantiomer of Formula (Ic) predominates:

37. The method of claim 36 wherein the enantiomer of Formula (Ic) predominates to the extent of about 90% or greater.

38. The method of claim 36 wherein the enantiomer of Formula (Ic) predominates to the extent of about 98% or greater.

39. The method of claim 1 wherein the method is a method for slowing or delaying the progression of neuropathic pain and cluster headache-associated pain comprising administering to a subject in need thereof a therapeutically effective amount of a compound of Formula (I).

40. The method of claims 3, 7, 10, 32, 36 or 39 wherein the therapeutically effective amount is from 0.01 mg/Kg/dose to about 100 mg/Kg/dose.

* * * * *